(12) United States Patent
Bharadwaj et al.

(10) Patent No.: US 7,670,342 B2
(45) Date of Patent: Mar. 2, 2010

(54) OSTEOCHONDRAL IMPLANT PROCEDURE AND DEVICE

(75) Inventors: Jeetendra Bharadwaj, Memphis, TN (US); Carlos E. Gil, Collierville, TN (US); Daniel Shimko, Collierville, TN (US); Eric Weeks, Millington, TN (US)

(73) Assignee: Warsaw Orthopedic, Inc.

( * ) Notice: Subject to any disclaimer, the term of this patent is extended or adjusted under 35 U.S.C. 154(b) by 449 days.

(21) Appl. No.: 11/338,926

(22) Filed: Jan. 25, 2006

(65) Prior Publication Data

US 2007/0173846 A1 Jul. 26, 2007

(51) Int. Cl.
*A61B 17/00* (2006.01)
(52) U.S. Cl. .......................................... 606/79
(58) Field of Classification Search ............... 606/79, 606/80, 82, 83, 84, 86 R, 88, 89; 33/227, 33/263, 628, 638, 286; 83/515, 669
See application file for complete search history.

(56) References Cited

U.S. PATENT DOCUMENTS

| | | | | | |
|---|---|---|---|---|---|
| 4,078,869 | A | * | 3/1978 | Honeycutt | 408/16 |
| 4,126,136 | A | * | 11/1978 | Auth et al. | 606/3 |
| 4,150,675 | A | * | 4/1979 | Comparetto | 606/84 |
| 4,487,209 | A | * | 12/1984 | Mehl | 600/567 |
| 4,627,435 | A | * | 12/1986 | Hoskin | 606/28 |
| 4,649,918 | A | * | 3/1987 | Pegg et al. | 606/79 |
| 4,832,045 | A | * | 5/1989 | Goldberger | 600/567 |
| 4,982,103 | A | * | 1/1991 | Meiffren et al. | 250/559.13 |
| 5,123,907 | A | * | 6/1992 | Romaine | 606/131 |
| 5,183,053 | A | * | 2/1993 | Yeh et al. | 600/567 |
| 5,446,635 | A | * | 8/1995 | Jehn | 362/259 |
| 5,792,163 | A | * | 8/1998 | Hitzig | 606/167 |
| 5,827,199 | A | * | 10/1998 | Alexander | 600/564 |
| 5,848,978 | A | * | 12/1998 | Cecchi | 600/567 |
| 5,957,946 | A | * | 9/1999 | Shuler et al. | 606/184 |
| 5,961,522 | A | * | 10/1999 | Mehdizadeh | 606/79 |
| 6,155,989 | A | * | 12/2000 | Collins | 600/565 |
| 6,306,142 | B1 | * | 10/2001 | Johanson et al. | 606/79 |
| 6,383,179 | B1 | * | 5/2002 | Neuberger | 606/16 |
| 6,584,695 | B1 | * | 7/2003 | Chang | 30/391 |
| 6,878,954 | B2 | * | 4/2005 | Butler et al. | 250/559.3 |
| D518,178 | S | * | 3/2006 | Christiansen | D24/147 |
| 7,055,252 | B2 | * | 6/2006 | Wu | 33/286 |
| 7,140,118 | B2 | * | 11/2006 | Adrian | 33/286 |
| 7,369,916 | B2 | * | 5/2008 | Etter et al. | 700/160 |

(Continued)

FOREIGN PATENT DOCUMENTS

JP 2007030014 A * 2/2007

OTHER PUBLICATIONS

U.S. Appl. No. 11/340,024, filed Jan. 26, 2006, Nycz et al.
U.S. Appl. No. 11/339,194, filed Jan. 25, 2006, Nycz et al.
U.S. Appl. No. 11/317,985, filed Dec. 23, 2005, Lyons.

(Continued)

*Primary Examiner*—Eduardo C Robert
*Assistant Examiner*—Ellen Rust

(57) ABSTRACT

A surgical procedure according to which a cutting blade is positioned over an area of the bone to be cut and indicia is projected onto the area. The blade is adjusted relative to the area until the indicia takes a predetermined configuration on the area corresponding to the desired position of the blade relative to the area. Then the blade can be driven to cut an opening in the bone.

21 Claims, 3 Drawing Sheets

U.S. PATENT DOCUMENTS

| | | | | |
|---|---|---|---|---|
| 7,510,557 | B1 * | 3/2009 | Bonutti | 606/86 R |
| 2005/0284942 | A1 * | 12/2005 | Gurevich et al. | 235/462.21 |
| 2006/0218788 | A1 * | 10/2006 | Boulnois et al. | 29/889.72 |
| 2007/0149982 | A1 * | 6/2007 | Lyons | 606/99 |

OTHER PUBLICATIONS

U.S. Appl. No. 11/340,884, filed Jan. 27, 2006, Shimko et al.
U.S. Appl. No. 11/343,156, filed Jan. 30, 2006, Bharadwaj et al.
U.S. Appl. No. 11/339,694, filed Jan. 25, 2006, Gil.

* cited by examiner

OSTEOCHONDRAL IMPLANT PROCEDURE AND DEVICE

BACKGROUND

This invention relates to an improved osteochondral implant procedure and device, and more particularly, to such a procedure and device in which a recipient opening is prepared for receiving a graft.

In the human body, the knee consists of three bones—a femur, a tibia, and a patella—that are held in place by various ligaments. The corresponding chondral areas of the femur and the tibia form a hinge joint, and the patella protects the joint. Portions of the latter areas, as well as the underside of the patella, are covered with an articular cartilage, which allow the femur and the tibia to smoothly glide against each other without causing damage.

The articular cartilage often tears, usually due to traumatic injury (often seen in athletics) and degenerative processes (seen in older patients). This tearing does not heal well due to the lack of nerves, blood vessels and lymphatic systems; and the resultant knee pain, swelling and limited motion of the bone(s) must be addressed.

Damaged adult cartilages have historically been treated by a variety of surgical interventions including lavage, arthroscopic debridement, and repair stimulation, all of which provide less than optimum results.

Another known treatment involves removal and replacement of the damaged cartilage with a prosthetic device. However, the known artificial prostheses have largely been unsuccessful since they are deficient in the elastic, and therefore in the shock-absorbing, properties characteristic of the cartilage. Moreover, the known artificial devices have not proven able to withstand the forces inherent to routine knee joint function.

In an attempt to overcome the problems associated with the above techniques, osteochondral transplantation, also known as "mosaicplasty" has been used to repair articular cartilages. This procedure involves removing injured tissue from the damaged area and drilling openings in the underlying bone. One or more plugs, consisting of healthy cartilage overlying bone, are obtained from another area of the patient, typically from a lower weight-bearing region of the joint under repair, or from a donor patient, and are implanted in the openings. In order to insure a precise fit between the plug and the opening, it is important that the opening is perpendicular to the plane of the bone. However, the curvature of the condyle of the fibia makes this difficult.

An embodiment of the present invention involves a technique for insuring that the opening formed in the bone to receive the plug extends perpendicularly to the plane of the bone.

DETAILED DESCRIPTION

Figure 1:
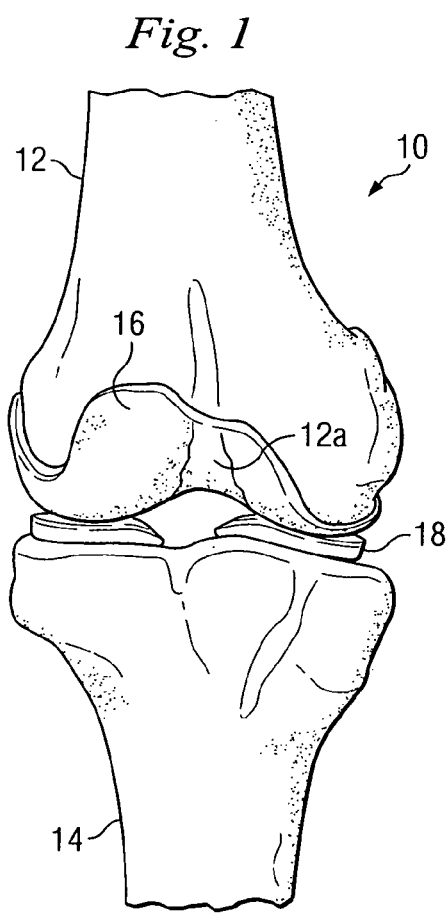
FIG. 1 is an elevational view of a human knee with certain parts removed in the interest of clarity.

Referring to FIG. 1 of the drawing, the reference numeral 10 refers, in general, to a knee area of a human including a femur 12 and a tibia 14 whose respective chondral areas are in close proximity. A cartilage 16 extends over a portion of the chondral area of the femur 12, and a meniscus 18 extends between the cartilage and the tibia 14. The patella, as well as the tendons, ligaments, and quadriceps that also form part of the knee, are not shown in the interest of clarity.

Figure 2:
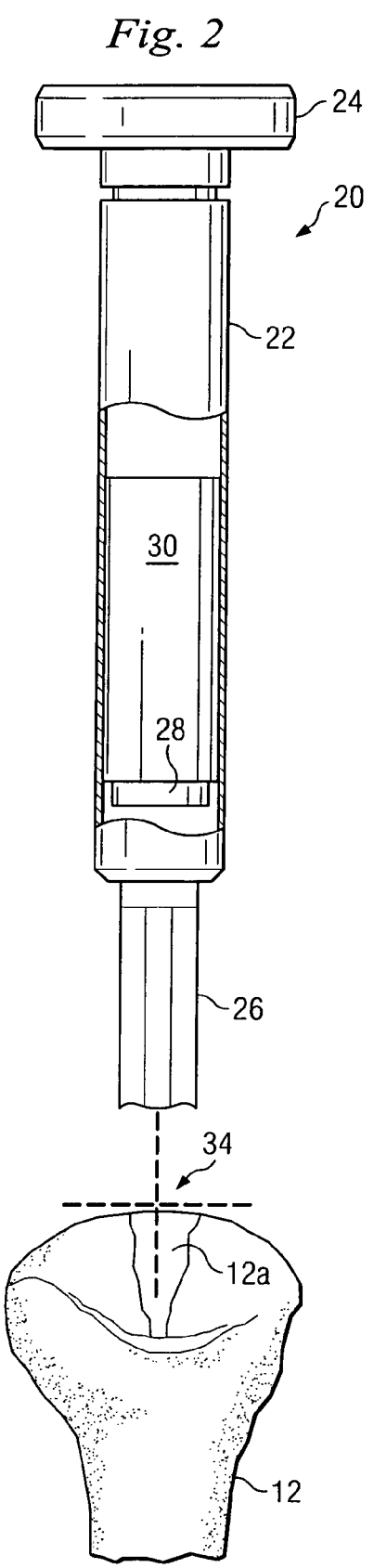
FIG. 2 is an exploded, partial sectional-partial elevational view of a chisel extending over the femur of the knee of FIG. 1 and depicting a laser beam projecting from the chisel onto the femur.

Referring to FIG. 2 which depicts the femur 12 of FIG. 1 in an inverted position, it will be assumed that a portion of the cartilage 16 extending over a chrondral area of the femur 12, has been damaged and removed by the surgeon, or has worn away, leaving a damaged area, or defect 12a. It will also be assumed that it is desired to create an opening, or series of openings, extending from the condyle of the defect 12a into the corresponding chondral area of the femur 12 to receive a graft or grafts.

It is understood that one or more grafts are harvested from another area of the patient/recipient, such as an undamaged non-load bearing area of the femur or tibia, or from a corresponding area of a donor, in accordance with known techniques. These grafts are sized so as to be implantable in the above openings in accordance with the following.

Figure 3:
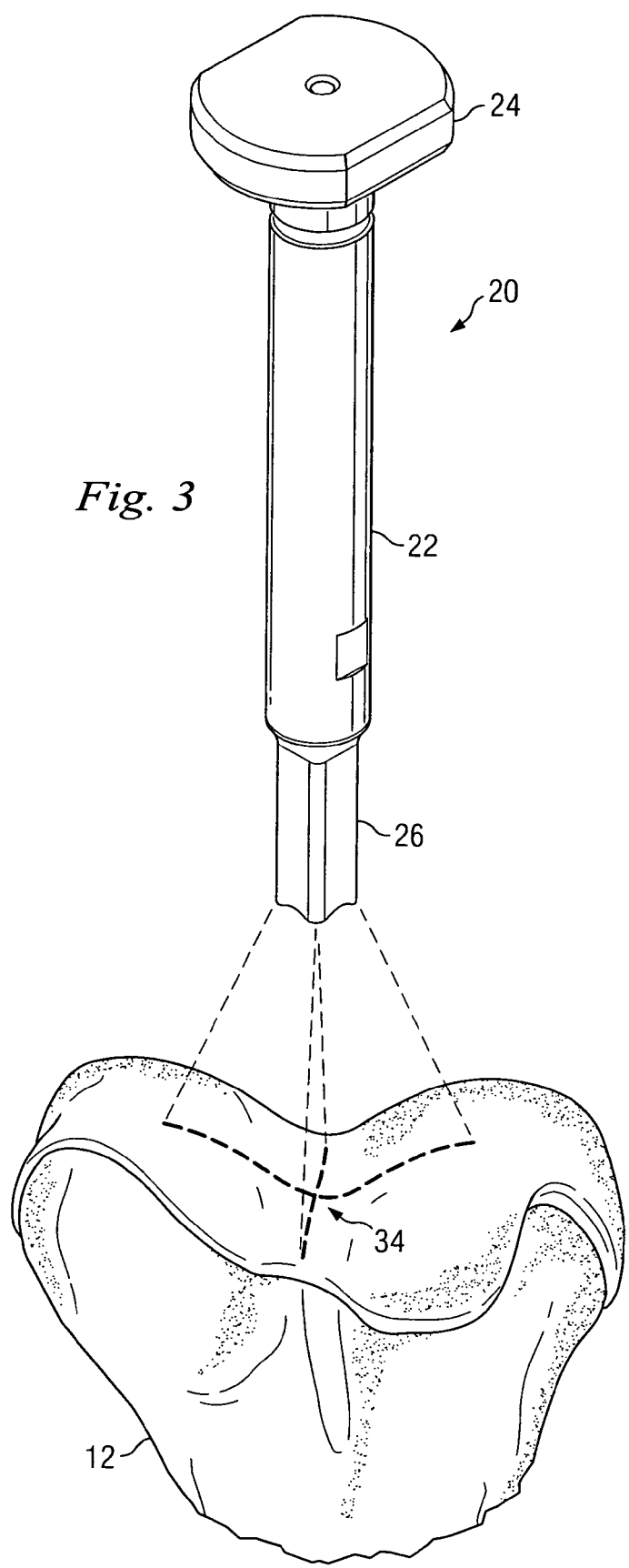
FIG. 3 is an isometric view of the chisel and femur of FIG. 2.

Referring to FIGS. 2 and 3, a chisel system is referred to, in general, by the reference numeral 20 and includes a hollow cylindrical body member 22 having a handle 24 formed integrally with the body member, or attached to the body member in any conventional manner.

The chisel system 20 is shown in proximity to the femur and, for the convenience of presentation, the femur 12 is shown inverted from the position shown in FIG. 1. The chisel system 20 also includes a hollow blade 26 extending from the other end of the body member 22 which can be of the type disclosed in co-pending U.S. patent application Ser. No. 11/343,156 now U.S. Pat. No. 7,497,861. The blade 26 can be formed integrally with the body member 22, or it can be attached to the body member in any conventional manner. The cross section of the blade 26 can take any configuration corresponding to the cross-section of the plug to be implanted, and for the purpose of example, it will be assumed that the cross-section of the blade 26 is rectangular.

Inasmuch as the surface of the defect 12a is curved, it is a challenge to insure that the blade 26 extends perpendicularly to the plane of the defect before the above opening is cut by the blade. To this end, a laser system is provided in the body member 22 and consists of a laser beam projector 28 supported at one end of the housing 30 which, in turn, is mounted in the interior of the body member 22. The housing 30 contains electronics associated with the operation of the projector 28.

The projector 28 is located in the end portion of the body member 22 adjacent the blade 26 and, when activated by a simple switch (not shown), or the like, associated with the body member, is adapted to project indicia shown, in general, by the reference numeral 34, and described in detail later, onto the defect 12a. The laser system will not be described in any further detail since it is conventional and could be in the form of the model PLS$^2$ Palm Laser manufactured by Pacific Laser Systems of Sausalito, Calif.

Figure 4A:
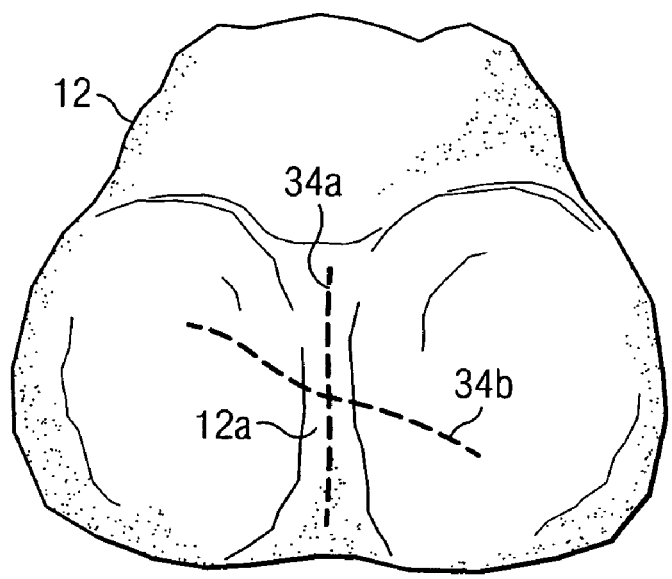
FIGS. 4a and 4b depict two different projections of the laser beam onto the surface of the femur.
Figure 4B:
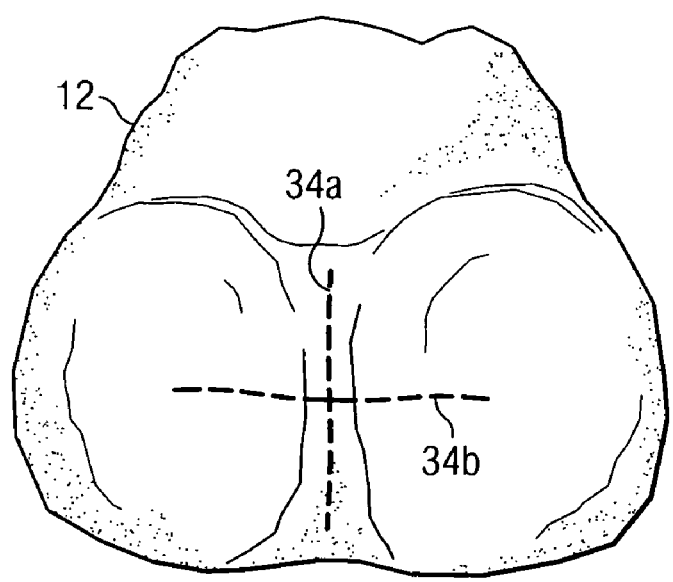

As better shown in FIGS. 4a and 4b, the projector projects indicia 34, which takes the form of a crosshair, consisting of two mutually perpendicular lines 34a and 34b, when projected onto a flat surface that is perpendicular to the axis of the projector. FIG. 4a depicts the lines 34a and 34b when the axes of the projector 28, and therefore the blade 26 of the chisel system 20, are not perpendicular to the plane of the defect 12a. This is manifested by the line 34b not being horizontal and therefore not being perpendicular to the line 34a, but rather indicates that the blade 34a is tilted slightly in one plane from a perfectly perpendicular position.

FIG. 4b depicts the lines 34a and 34b when the blade 26 is perpendicular to the plane of the femur 12. This is manifested by the lines 34a and 34b extending perpendicular to each other, with line 34a extending vertically (as viewed in the drawing), and line 34b extending horizontally. With this projection, the surgeon is insured that the blade 26 is perpendicular to the plane of the femur so that, when the blade is advanced to the defect 12a and driven into the femur, an opening is cut in the femur that is perpendicular to the plane of the defect. Therefore when the above-mentioned graft is inserted in the opening, the cartilage portion of the graft is located in substantially the same position as the original damaged cartilage.

In operation, the chisel system 10 is positioned near the defect 12a with the distal end of the blade extending adjacent the defect. The projector 30 is activated to project the indicia 34 on the defect 12a. The angular position of the chisel system 20, and therefore the axis of the projector 28 and the blade 26 relative to the defect 12a, is adjusted until the lines 34a and 34b extend perpendicular to each other as shown in FIG. 4b. The blade 26 is then driven into the femur 12 to cut an opening in the femur that is perpendicular to the plane of the defect 12a. Therefore, when the above-mentioned graft is inserted in the opening, it will also extend perpendicular to the plane of the femur with the cartilage portion of the graft located in substantially the same position as the original damaged cartilage.

Variations

1. The shape and dimensions of the blade 26 can vary within the scope of the invention. For example, the blade 26, and therefore the opening to be cut, can have a circular cross section.

2. The form of the indicia 34 projected by the projector 28 can vary. Examples include a circle, a single line, two or more parallel lines, a square, two or more concentric circles, a dot matrix, etc.

3. The desired position of the blade relative to the defect can be a position other than the perpendicular position discussed above. For example, it may be desired to cut an opening in the femur 12 that extends at an angle to the plane of the defect, in which case the indicia would be changed accordingly.

3. The spatial references mentioned above, such as "upper", "lower", "under", "over", "between", "outer", "inner" and "surrounding" are for the purpose of illustration only and do not limit the specific orientation or location of the components described above.

Those skilled in the art will readily appreciate that many other variations and modifications of the embodiment described above can be made without materially departing from the novel teachings and advantages of this invention. Accordingly, all such variations and modifications are intended to be included within the scope of this invention as defined in the following claims. In the claims, means-plus-function clauses are intended to cover the structures described herein as performing the recited function and not only structural equivalents, but also equivalent structures.

What is claimed is:

1. A surgical device for extracting a tissue graft from a tissue, the device comprising:

a shaft extending along a longitudinal axis between a proximal portion and a distal portion;

a handle extending from the proximal portion of the shaft;

a cutting module extending from the distal portion of the shaft, the cutting module comprising a chisel having an inner bore extending substantially along the longitudinal axis of the shaft and bounded distally by a cutting edge removably engaged with the shaft for longitudinal and non-rotational penetration of the tissue and extraction of the tissue graft, the inner bore sized and shaped for receiving the tissue graft cut from the tissue by the cutting edge; and a laser system positioned at least partially within the distal portion of the shaft, the laser system comprising a laser projector for projecting laser indicia distally through the inner bore of the cutting module and onto a surface of the tissue for determining an orientation of the longitudinal axis relative to the surface of the tissue, the laser indicia being a crosshair comprised of a first line extending in a first direction and a second line extending in a second direction substantially perpendicular to the first direction such that when the longitudinal axis of the shaft extends substantially perpendicular to a plane defined by the surface of the tissue the first and second lines extend substantially perpendicular to one another as viewed on the surface of the tissue and when the longitudinal axis of the shaft does not extend substantially perpendicular to the plane defined by the surface of the tissue the first and second lines do not extend substantially perpendicular to one another as viewed on the surface of the tissue, wherein the laser system further comprises a housing containing electronics of the laser systems, and wherein the housing mounted within an interior section of the distal portion of the shaft;

wherein the intersection of the first and second lines of the laser indicia is substantially in line with the longitudinal axis.

2. The device of claim 1, wherein the inner bore of the cutting module is sized and shaped for receiving a tissue graft comprising healthy cartilage overlying bone cut from a femur.

3. The device of claim 2, wherein the cutting module is integrally formed with the shaft.

4. The device of claim 3, wherein the handle is integrally formed with the shaft.

5. The device of claim 4, wherein the laser projector is selectively activatable by a user.

6. The device of claim 1 wherein the chisel has a non-circular cross-section.

7. The device of claim 6 wherein the non-circular cross section is rectangular.

8. A surgical device for extracting a graft of tissue in a direction substantially perpendicular to a surface of the tissue, the device comprising:

a shaft extending along a longitudinal axis between a proximal portion and a distal portion, the proximal portion of the shaft defining a handle for grasping by a user;

a cutting module extending substantially along the longitudinal axis of the shaft, the cutting module comprising a chisel having an inner bore extending substantially along the longitudinal axis of the shaft and bounded distally by a cutting edge removably engaged with the shaft for longitudinal and non-rotational penetration of the tissue and extraction of the tissue graft, the cutting edge defining a cutting profile of the cutting module, the inner bore sized and shaped for receiving the graft cut from the tissue by the cutting edge; and a laser system positioned at least partially within the distal portion of the shaft, the laser system comprising a laser projector for projecting laser indicia distally through the inner bore of the cutting module and onto a surface of the tissue for determining an orientation of the longitudinal axis relative to the surface of the tissue, the laser projector projecting at least a portion of the laser indicia onto the surface within the cutting profile of the cutting module, the laser indicia being a first line extending in a first direction and a second line extending in a second direction substantially parallel to the first direction such that when the longitudinal axis of the shaft extends substantially perpendicular to the surface of the tissue the first and second lines extend substantially parallel to one another as viewed on the surface of the tissue and when the longitudinal axis of the shaft does not extend substantially perpendicular to the plane defined by the surface of the tissue the first and second lines do not extend substantially parallel to one another as viewed on the surface of the tissue.

9. The device of claim 8, wherein the laser system is entirely mounted within the shaft.

10. The device of claim 9, wherein the cutting edge comprises a circular cross-section for cutting cylindrical grafts.

11. The device of claim 10, wherein the cutting module is integrally formed with the shaft.

12. The device of claim 8 wherein the chisel has a non-circular cross-section.

13. The device of claim 12 wherein the non-circular cross section is rectangular.

14. A surgical device for extracting a tissue graft from a tissue, the device comprising:
  a shaft extending along a longitudinal axis between a proximal portion and a distal portion;
  a handle extending from the proximal portion of the shaft;
  a cutting module extending from the distal portion of the shaft, the cutting module comprising a chisel having an inner bore extending substantially along the longitudinal axis of the shaft and bounded distally by a cutting edge removably engaged with the shaft for longitudinal and non-rotational penetration of the tissue and extraction of the tissue graft, the cutting edge defining a cutting profile of the cutting module, the inner bore sized and shaped for receiving the tissue graft cut from the tissue by the cutting edge; and
  a laser system positioned at least partially within the distal portion of the shaft, the laser system comprising a laser projector for projecting laser indicia distally through the inner bore of the cutting module and onto a surface of the tissue for determining an orientation of the longitudinal axis relative to the surface of the tissue, the laser projector projecting at least a portion of the laser indicia onto the surface within the cutting profile of the cutting module, the laser indicia being a plurality of concentric circles centered about the longitudinal axis such that when the longitudinal axis of the shaft extends substantially perpendicular to a plane defined by the surface of the tissue the concentric circles extend substantially concentrically to one another as viewed on the surface of the tissue and when the longitudinal axis of the shaft does not extend substantially perpendicular to the plane defined by the surface of the tissue the plurality of concentric circles do not extend substantially concentrically to one another as viewed on the surface of the tissue.

15. The device of claim 14, wherein a housing of the laser system is mounted within an interior section of the distal portion of the shaft.

16. The device of claim 15, wherein the inner bore of the cutting module is sized and shaped for receiving a tissue graft comprising healthy cartilage overlying bone cut from a femur.

17. The device of claim 16, wherein the cutting module is integrally formed with the shaft.

18. The device of claim 17, wherein the handle is integrally formed with the shaft.

19. The device of claim 18, wherein the cutting edge comprises a circular cross-section for cutting cylindrical tissue grafts.

20. The device of claim 14 wherein the chisel has a non-circular cross-section.

21. The device of claim 14 wherein the non-circular cross section is rectangular.

* * * * *